(12) United States Patent
Vulcu

(10) Patent No.: US 10,926,773 B2
(45) Date of Patent: Feb. 23, 2021

(54) SYSTEMS AND METHODS FOR MITIGATING MOTION SICKNESS IN A VEHICLE

(71) Applicants: Denso International America, Inc., Southfield, MI (US); Denso Corporation, Kariya (JP)

(72) Inventor: Victor George Vulcu, Royal Oak, MI (US)

(73) Assignees: Denso International America, Inc., Southfield, MI (US); Denso Corporation, Kariya (JP)

(*) Notice: Subject to any disclaimer, the term of this patent is extended or adjusted under 35 U.S.C. 154(b) by 0 days.

(21) Appl. No.: 16/409,240

(22) Filed: May 10, 2019

(65) Prior Publication Data

US 2020/0353934 A1 Nov. 12, 2020

(51) Int. Cl.
| | |
|---|---|
| *B60W 40/08* | (2012.01) |
| *G06F 3/01* | (2006.01) |
| *A61B 5/00* | (2006.01) |
| *A61B 5/024* | (2006.01) |
| *B60W 50/00* | (2006.01) |

(52) U.S. Cl.
CPC ............ *B60W 40/08* (2013.01); *A61B 5/024* (2013.01); *A61B 5/6893* (2013.01); *B60W 50/0098* (2013.01); *G06F 3/011* (2013.01); B60R 2300/8006 (2013.01); B60W 2040/0818 (2013.01); B60W 2040/0872 (2013.01); B60W 2420/42 (2013.01); B60W 2540/26 (2013.01)

(58) Field of Classification Search
CPC ............ B60W 40/08; B60W 50/0098; B60W 2540/26; B60W 2420/42; B60W 2040/0872; B60W 2040/0818; G06F 3/011; A61B 5/024; A61B 5/6893; B60R 2300/8006
See application file for complete search history.

(56) References Cited

U.S. PATENT DOCUMENTS

| | | | |
|---|---|---|---|
| 9,862,312 B2 | 1/2018 | Sivak et al. | |
| 9,868,332 B2 | 1/2018 | Anderson et al. | |
| 2009/0164073 A1* | 6/2009 | Mabuchi | .................. B60N 2/14 701/49 |
| 2014/0176296 A1 | 6/2014 | Morgan | |
| 2017/0136842 A1* | 5/2017 | Anderson | .......... B60G 17/0195 |

(Continued)

FOREIGN PATENT DOCUMENTS

| | | |
|---|---|---|
| CN | 201534508 | 7/2010 |
| JP | 2005075286 A | 3/2005 |
| WO | 2016126522 A1 | 8/2016 |

*Primary Examiner* — James J Yang
(74) *Attorney, Agent, or Firm* — Christopher G. Darrow; Darrow Mustafa PC

(57) ABSTRACT

System, methods, and other embodiments described herein relate to mitigating effects of motion sickness on a passenger in a vehicle. In one embodiment, a method includes analyzing sensor data about the passenger to produce a passenger state that characterizes a current physical condition of the passenger while riding in the vehicle. The method includes determining whether the passenger state correlates with symptoms of motion sickness in the passenger. The method includes controlling, in the vehicle, a vehicle component to adjust a current configuration relative to the passenger when the passenger state correlates with the symptoms.

17 Claims, 5 Drawing Sheets

(56) References Cited

U.S. PATENT DOCUMENTS

| | | | |
|---|---|---|---|
| 2018/0037093 A1* | 2/2018 | Newman | B60H 3/0078 |
| 2018/0222490 A1* | 8/2018 | Ishihara | B60W 50/14 |
| 2019/0047498 A1* | 2/2019 | Alcaidinho | G06F 3/14 |
| 2019/0357834 A1* | 11/2019 | Aarts | G08B 21/06 |

* cited by examiner

SYSTEMS AND METHODS FOR MITIGATING MOTION SICKNESS IN A VEHICLE

TECHNICAL FIELD

The subject matter described herein relates in general to systems and methods for mitigating motion sickness in a passenger of a vehicle and, more particularly, to selectively controlling various components of the vehicle when the vehicle detects motion sickness or the onset of motion sickness in the passenger.

BACKGROUND

Motion sickness affects a significant portion of the population. Some reports indicate that motion sickness affects nearly one-third of people on a regular basis and up to two-thirds of people in more severe instances. In general, motion sickness results from a conflict of sensory perceptions involving inputs from visual senses and vestibular systems. That is, when a visual frame of reference (e.g., no sensed motion) conflicts with vestibular sensations (i.e., sensed motion), a person may experience symptoms of motion sickness such as nausea, dizziness, headaches, and so on.

By way of example, occurrences of motion sickness more commonly result when a person is reading a book in a moving vehicle, or performing some other task that involves the person not observing the motion of the vehicle relative to the surrounding environment. Accordingly, as individuals become more consumed with personal devices (e.g., smartphones, tablets, etc.), which autonomous vehicles may facilitate since less interaction is necessary for driving, the occurrence of motion sickness among passengers may increase. Moreover, traditional approaches to preventing motion sickness generally include preventative approaches such as the use of medicines. However, the efficacy of such medicine can be limited to certain individuals and also necessitates forethought to have the medicine on hand and to use the medicine. Therefore, present approaches to preventing motion sickness may be limited.

SUMMARY

In one embodiment, example systems and methods associated with mitigating motion sickness of a passenger in a vehicle are disclosed. As previously noted, many people may suffer from motion sickness when riding in a vehicle. Moreover, with the prevalence of personal electronic devices and other distractions that direct the attention of passengers away from an environment around the vehicle, the likelihood of the occurrence of sensory conflict that induces motion sickness may be higher. However, the difficulties associated with present approaches to preventing motion sickness result in motion sickness remaining a common occurrence among passengers of vehicles.

Therefore, in one embodiment, a motion system is disclosed that monitors a passenger of a vehicle for signs of motion sickness. Thus, the motion system can, in one approach, automatically control one or more components of a vehicle to mitigate motion sickness when detected in the passenger. In this way, the motion system provides for improving mitigation/avoidance of motion sickness in passengers.

In one embodiment, a motion system for mitigating motion sickness in a passenger of a vehicle is disclosed. The motion system includes one or more processors and a memory that is communicably coupled to the one or more processors. The memory stores a passenger module module including instructions that when executed by the one or more processors cause the one or more processors to analyze sensor data about the passenger to produce a passenger state that characterizes a current physical condition of the passenger while riding in the vehicle. The passenger module includes instructions to determine whether the passenger state correlates with symptoms of motion sickness in the passenger. The memory stores a control module including instructions that when executed by the one or more processors cause the one or more processors to control, in the vehicle, a vehicle component to adjust a current configuration relative to the passenger when the passenger state correlates with the symptoms.

In one embodiment, a non-transitory computer-readable medium is disclosed. The computer-readable medium stores instructions that when executed by one or more processors cause the one or more processors to perform the disclosed functions. The instructions include instructions to analyze sensor data about the passenger to produce a passenger state that characterizes a current physical condition of the passenger while riding in the vehicle. The instructions include instructions to determine whether the passenger state correlates with symptoms of motion sickness in the passenger. The instructions include instructions to control, in the vehicle, a vehicle component to adjust a current configuration relative to the passenger when the passenger state correlates with the symptoms.

In one embodiment, a method of mitigating motion sickness in a passenger of a vehicle. In one embodiment, the method includes analyzing sensor data about the passenger to produce a passenger state that characterizes a current physical condition of the passenger while riding in the vehicle. The method includes determining whether the passenger state correlates with symptoms of motion sickness in the passenger. The method includes controlling, in the vehicle, a vehicle component to adjust a current configuration relative to the passenger when the passenger state correlates with the symptoms.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

DETAILED DESCRIPTION

Figure 1:
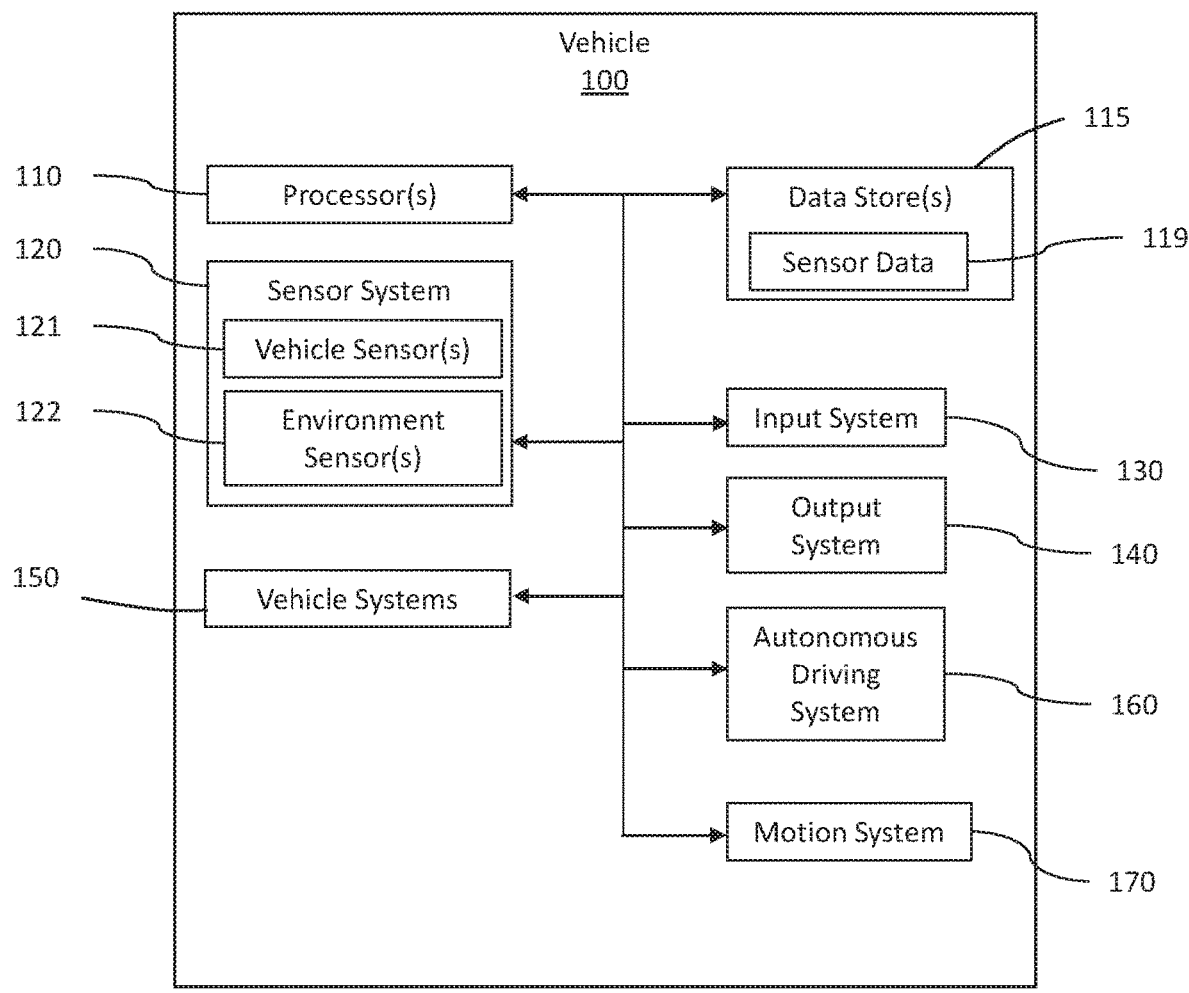
FIG. 1 illustrates one embodiment of a configuration of a vehicle in which example systems and methods disclosed herein may operate.

Systems, methods, and other embodiments associated with mitigating motion sickness in a passenger of a vehicle are disclosed. As previously noted, many people may suffer from motion sickness when riding in a vehicle. Moreover, with the prevalence of distractions (e.g., personal electronic devices, video monitors, etc.) that direct the attention of passengers away from an environment around the vehicle, the likelihood of sensory conflict that induces motion sickness may be higher. However, difficulties (e.g., efficacy, availability, etc.) associated with present approaches to preventing motion sickness, result in motion sickness remaining a common occurrence among passengers of vehicles.

Therefore, in one embodiment, a motion system is disclosed that performs various tasks to actively prevent or otherwise mitigate motion sickness in a passenger. For example, in one approach, the motion system monitors a passenger (or multiple passengers) of a vehicle through the use of sensors that acquire sensor data indicating information about the passenger. In one embodiment, the motion system includes a wearable sensor that is worn by the passenger (e.g., on a wrist, around the chest, etc.). The wearable sensor communicates sensor data to the motion system that includes, for example, observations of vital signs of the passenger and/or other information that the motion system uses to produce a passenger state. Additionally, or alternatively, the motion system, in one or more embodiments, acquires the sensor data from sensors integrated within a passenger compartment of the vehicle such as cameras, heart rate monitors, and so on. The sensors integrated within the passenger compartment may be integrated into a seat or other suitable locations to collect the sensor data.

The motion system analyzes the sensor data to produce, for example, the passenger state that characterizes a physical condition of the passenger. Thus, the passenger state may indicate whether the passenger is experiencing motion sickness or the onset of motion sickness through the definition of the various aspects (e.g., vital signs) about the passenger. Therefore, the motion system, in one approach, generates the passenger state as an assessment of the physical condition of the passenger over a defined period of time. As such, the motion system can then, for example, determine whether the passenger is exhibiting symptoms of motion sickness. In one embodiment, the motion system compares the passenger state (e.g., changes in heart rate, blood pressure, breathing rate, etc.) to the known symptoms associated with motion sickness. If the motion system determines that the passenger state corresponds with the symptoms within, for example, at least a threshold variation, then the motion system indicates that the passenger is experiencing motion sickness or the onset of motion sickness and may then execute one or more actions in response.

In one embodiment, in response to identifying that the passenger state corresponds with the symptoms of motion sickness, the motion system automatically controls a vehicle component such as a seat of the passenger to adjust in a way that mitigates the symptoms in the passenger. That is, for example, if the motion system determines that the passenger is experiencing motion sickness, then the motion system can recline the seat of the passenger so that the passenger can lay in a supine position. Such a change in physical position for the passenger can help to reduce the symptoms and resolve the motion sickness. Moreover, in various embodiments, the motion system can be implemented to control different vehicle systems and/or combinations of systems.

By way of example, the motion system, in various approaches, controls the seat of the passenger to recline, to adjust seating ventilation (e.g., heating/cooling), to adjust lumbar support, height, forward/back position, headrest position, and so on. Moreover, the motion system can also be implemented to control heating, ventilation, and air condition (HVAC) systems to adjust temperature, fan speeds, air source, ionization, and so on. In still further aspects, the motion system controls positions of windows, infotainment (e.g., volume, media source, etc.), displays, and so on. In controlling displays of the vehicle, the motion system can cause the displays to render particular graphics such as a marker/point of focus for the passenger at a horizon line, and/or other visuals that can facilitate mitigating the symptoms of motion sickness in the passenger. In this way, the motion system actively monitors the passenger state and provides mitigating/preventative actions by controlling the one or more vehicle components/systems to influence the passenger and offset or resolve the motion sickness.

Referring to FIG. 1, an example of a vehicle 100 is illustrated. As used herein, a "vehicle" is any form of powered transport. In one or more implementations, the vehicle 100 is an automobile. While arrangements will be described herein with respect to automobiles, it will be understood that embodiments are not limited to automobiles. In some implementations, the vehicle 100 may be any robotic device or form of powered transport that, for example, carries passengers and thus benefits from the functionality discussed herein.

The vehicle 100 also includes various elements. It will be understood that in various embodiments the vehicle 100 may not have all of the elements shown in FIG. 1. The vehicle 100 can have different combinations of the various elements shown in FIG. 1. Further, the vehicle 100 can have additional elements to those shown in FIG. 1. In some arrangements, the vehicle 100 may be implemented without one or more of the elements shown in FIG. 1. While the various elements are shown as being located within the vehicle 100 in FIG. 1, it will be understood that one or more of these elements can be located external to the vehicle 100. Further, the elements shown may be physically separated by large distances and provided as remote services (e.g., cloud-computing services).

Some of the possible elements of the vehicle 100 are shown in FIG. 1 and will be described along with subsequent figures. A description of many of the elements in FIG. 1 will be provided after the discussion of FIGS. 2-5 for purposes of brevity of this description. Additionally, it will be appreciated that for simplicity and clarity of illustration, where appropriate, reference numerals have been repeated among the different figures to indicate corresponding, analogous, or similar elements. Furthermore, it should be understood that the embodiments described herein may be practiced using various combinations of the described elements. In either case, the vehicle 100 includes a motion system 170 that functions to mitigate motion sickness within passengers of the vehicle 100. The noted functions and methods will become more apparent with a further discussion of the figures.

Figure 2:
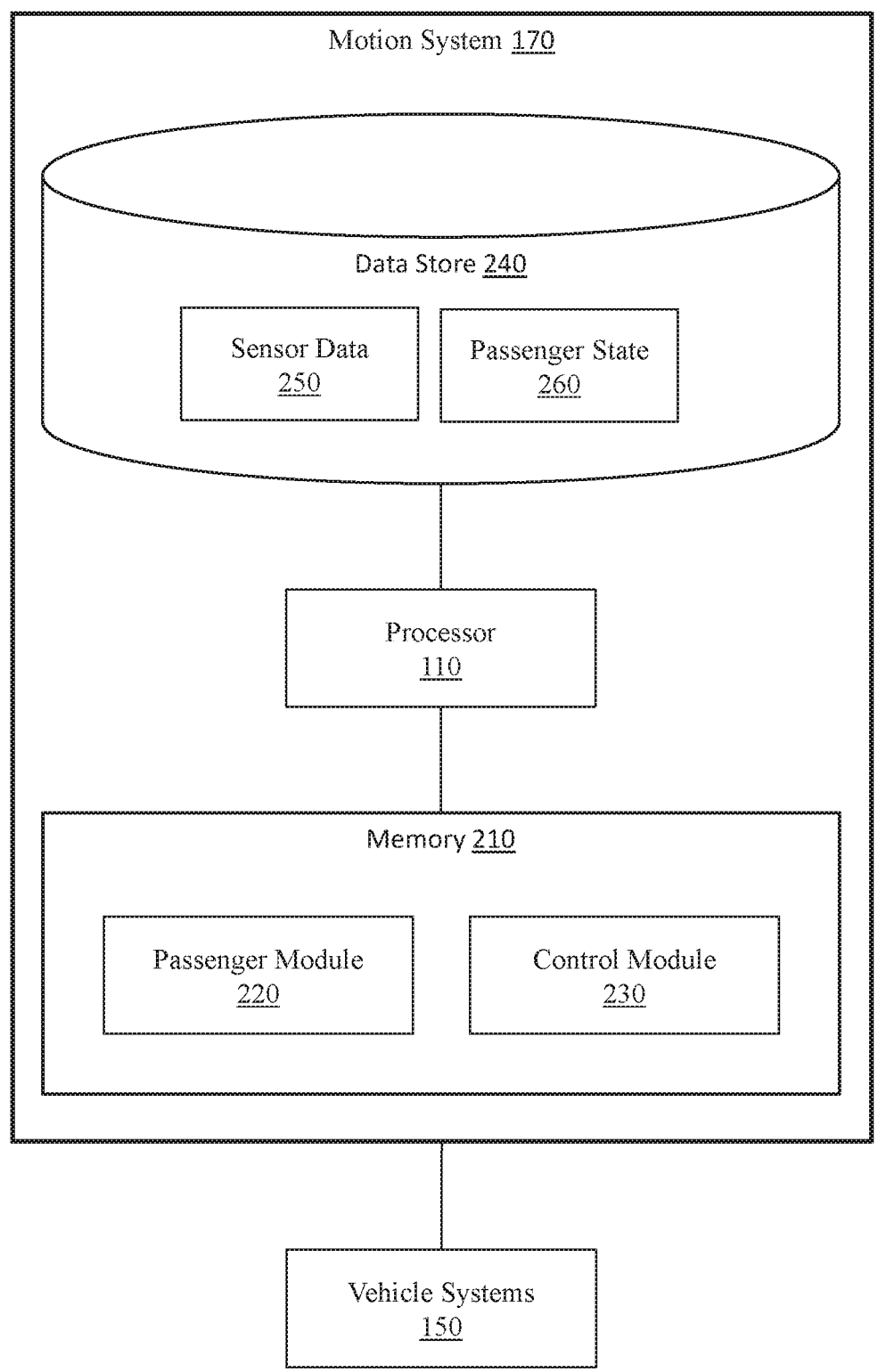
FIG. 2 illustrates one embodiment of a motion system that is associated with mitigating motion sickness.

With reference to FIG. 2, one embodiment of the motion system 170 is further illustrated. As shown, the motion system 170 includes a processor 110. Accordingly, the processor 110 may be a part of the motion system 170 or the motion system 170 may access the processor 110 through a data bus or another communication path. In one or more embodiments, the processor 110 is an application specific integrated circuit that is configured to implement functions associated with a passenger module 220 and a control module 230. In general, the processor 110 is an electronic processor such as a microprocessor that is capable of performing various functions as described herein. In one embodiment, the motion system 170 includes a memory 210 that stores the passenger module 220 and the control module 230. The memory 210 is a random-access memory (RAM), read-only memory (ROM), a hard disk drive, a flash memory, or other suitable memory for storing the modules 220 and 230. The modules 220 and 230 are, for example, computer-readable instructions that when executed by the processor 110 cause the processor 110 to perform the various functions disclosed herein. While, in one or more embodiments, the modules 220 and 230 are instructions embodied in the memory 210, in further aspects, the modules 220 and 230 include hardware such as processing components (e.g., controllers) for independently performing the noted functions.

Furthermore, in one embodiment, the motion system 170 includes a data store 240. The data store 240 is, in one embodiment, an electronically-based data structure for storing information. For example, in one approach, the data store 240 is a database that is stored in the memory 210 or another suitable medium, and that is configured with routines that can be executed by the processor 110 for analyzing stored data, providing stored data, organizing stored data, and so on. In either case, in one embodiment, the data store 240 stores data used by the modules 220 and 230 in executing various functions. In one embodiment, the data store 240 includes sensor data 250, and a passenger state 260 along with, for example, other information (e.g., symptoms, thresholds, etc.) that is used by the modules 220 and 230.

Accordingly, the passenger module 220 generally includes instructions that function to control the processor 110 to acquire data inputs from one or more sensors (e.g., sensor system 120) of the vehicle 100 that form the sensor data 250. In general, the sensor data 250 includes information that embodies observations of the interior passenger compartment of the vehicle 100 including the passenger(s). Thus, the observations embodied in the sensor data 250 can include, for example, information from seat sensors indicating seat position (e.g., recline, longitudinal position, height, etc.), a presence and/or a weight of a passenger, and so on.

The sensor data 250 can further include camera images providing information about various aspects of the passenger (e.g., a seating arrangement, a height, other physical condition indicating information (sweating)), and so on. In one or more arrangements, the passenger module 220 may process the sensor data 250 to derive further information about the passenger. For example, the passenger module 220 processes, in one approach, camera images of the passenger to determine breathing rate, heart rate, position (e.g., leaning, hunched over, etc.), and so on. The passenger module 220, in one embodiment, processes the camera images using, for example, one or more machine learning algorithms (e.g., convolutional neural networks (CNNs)) that provide for recognizing the passenger and information about the passenger such as the noted vital signs including heart rate, breathing rate, and so on.

Moreover, in one or more arrangements, the passenger module 220 acquires at least a portion of the sensor data 250 from sensors within the seat of the passenger or within close proximity to the passenger. For example, in one approach, the vehicle 100 may be configured with heart rate sensors in a seat back, in handles of a door, and so on. Additionally, the vehicle 100 may include gyroscopes (e.g., inertial measurements units (IMU)) to detect movement and patterns of movement of the vehicle 100 that may correlate within conditions (e.g., intensity, frequency, direction of movements, etc.) that induce motion sickness. In still further aspects, the vehicle 100 includes infrared cameras, temperature sensors, and other sensors that monitor the passenger and an internal environment of the vehicle 100 around the passenger.

In one or more arrangements, the passenger module 220 acquires information from one or more wearable sensors that, for example, are worn by a passenger and are in communication with the passenger module 220 through either a wired or wireless communication channel. In a further aspect, as used herein, a wearable sensor includes sensors that are implanted within the passenger. Accordingly, the implanting of a wearable sensor can include a sub-dermal implant or an implant that is placed further within a body of the passenger (e.g., within a muscle, onto a nerve, onto an organ—heart, brain, etc.). In general, a sensor worn by or implanted within the passenger can provide information such as perspiration rate, breathing rate, heart rate, blood pressure, blood oxygen levels, passenger body temperature, and so on. The worn sensor(s) may be worn around a wrist, the chest, an ankle, a leg, integrated with a piece of apparel (e.g., hat, glasses, etc.), implanted within the body, or otherwise generally in contact with the passenger so that the worn sensor can perceive information about the passenger to provide the sensor data.

It should be appreciated that the disclosed approach can be extended to cover further configurations of sensors such as multiple cameras, interior integrated sensors (e.g., in-seat), in combination with one or more worn sensors. Moreover, as a general matter, the passenger module 220, in one approach, acquires the sensor data 250 and processes (i.e., image recognition/analysis) the sensor data 250 to generate observations of the passenger. In alternative arrangements, the passenger module 220 functions cooperatively with other modules/systems in the vehicle 100. For example, the passenger module 220, in one approach, functions together with image recognition components of the autonomous driving system 160 or another module/system to implement various routines for performing the determination of the passenger state 260.

Accordingly, in one embodiment, the passenger module 220 controls the respective sensors to provide the data inputs in the form of the sensor data 250. Additionally, while the passenger module 220 is discussed as controlling the various sensors of the sensor system 120 and otherwise to provide the sensor data 250, in one or more embodiments, the passenger module 220 employs other techniques that are either active or passive to acquire the sensor data 250. The passenger module 220 may passively sniff the sensor data 250 from a stream of electronic information provided by the various sensors to further components within the vehicle 100. Moreover, the passenger module 220 can undertake various approaches to fuse data from multiple sensors when providing the sensor data 250 and/or from sensor data acquired over a wireless communication link (e.g., WiFi with the worn sensor). Thus, the sensor data 250, in one embodiment, represents a combination of observations acquired from multiple sensors.

The sensor data 250 itself generally provides information to identify the presence of a passenger and characteristics of the passenger (e.g., physical traits such as vital signs). Moreover, the passenger module 220, in one embodiment, controls the sensors to acquire the sensor data 250 about all seating areas inside of the vehicle 100 including, for example, a front passenger seat, a rear passenger seats, an operator seat, and so on. As such, the passenger module 220 can monitor multiple passengers simultaneously and passengers in different seating configurations. In one approach, the passenger module 220 monitors children seated in child safety seats for motion sickness. Whichever passenger the passenger module 220 is monitoring, the passenger module 220 generates a separate passenger state 260 according to the respective sensor data 250 and maintains/updates the passenger state(s) 260 as the passenger module 220 acquires new observations forming the sensor data 250. In this way, the motion system 170 actively monitors the passenger(s) to collect physical traits that provide for identifying that the passenger is experiencing or is about to experience motion sickness.

Moreover, with further reference to the passenger module 220 generally includes instructions that function to control the processor 110 to analyze the sensor data 250 about a passenger to generate the passenger state 260. In general, the passenger module 220 characterizes the sensor data 250 by, for example, extracting relevant information about the physical condition of the passenger for the sensor data 250 and characterizing the physical condition over a defined time period. For example, the passenger module 220, in one approach, characterizes the vital signs (e.g., heart rate, breathing rate) in combination with one or more other physical traits (e.g., perspiration) over the defined time period to assess changes/traits in the passenger that are indicative of motion sickness.

Thus, in one aspect, the passenger module 220 identifies changes in the noted physical traits over time (e.g., a sliding window of 30 seconds or another defined window). The particular time employed for characterizing the changes/traits may vary according to the underlying sensor data 250 being analyzed. For example, the passenger module 220 may calculate the heart rate over a thirty-second window of sensor data while characterizing changes over a longer period (e.g., minutes). Similarly, the passenger module 220 may characterize breathing rate, blood pressure, and so on over one period to define the trait and another to characterize changes in the trait. As another example, the passenger module 220 can characterize one or more traits in a discrete manner as a threshold determination. The passenger module 220 characterizes, in one aspect, the presence of perspiration or no perspiration, a heart rate above/below a threshold rate, breathing above/below a threshold rate, and so on. Accordingly, the passenger module 220 can be configured in a robust manner to characterize the passenger traits/conditions to derive the passenger state 260.

The passenger module 220 can then use the determination of the passenger state 260 to determine whether the passenger is experiencing motion sickness. That is, in one approach, the passenger module 220 determines whether the passenger state 260 correlates with symptoms of motion sickness in the passenger. Thus, in one approach, the passenger module 220 compares the passenger state 260 with known symptoms of motion sickness to determine when the passenger is experiencing or is about to experience motion sickness. The symptoms include, in one embodiment, increased heart rate, increased breathing rate, increased blood pressure, and perspiration. In further aspects, the symptoms may be defined to include threshold levels/rates for the various indicators such as, for example, above 80 bpm for heart rate. Moreover, while the symptoms are generally discussed as increases or in relation to threshold values, in various approaches, the passenger module 220 determines a baseline for one or more physical conditions of the passenger and actively defines the changes/thresholds therefrom.

For example, in one approach, the passenger module 220 detects the presence of a passenger inside of the vehicle 100 and then begins to monitor the passenger by collecting the sensor data 250 and generating the passenger state 260. The initial passenger state 260 may serve as a baseline representation of the physical condition of the passenger from which the passenger module 220 defines the baseline and/or thresholds. In either case, the passenger module 220 generates the passenger state 260 according to ongoing observations of the passenger and uses the defined symptoms as a point of comparison with the passenger state 260 to determine when the passenger is experiencing motion sickness.

Additionally, the passenger module 220, in one embodiment, detects the symptoms of motion sickness in the passenger as either an onset or a developed instance of motion sickness. That is, in one embodiment, the passenger module 220 monitors the passenger state 260 for the development of the symptoms over time and may indicate the onset of motion sickness. For example, the passenger module 220, in one approach, generates the passenger state 260 according to a baseline, as previously mentioned. As such, the passenger module 220 may define onset conditions as a progression of one or more components of the passenger state 260 in relation to the baseline toward a threshold. For example, the passenger module 220 may define the onset conditions as an increase in heart rate, an increase in breathing rate, an increase in blood pressure, etc.

However, the noted increases are generally not sufficient to satisfy a threshold associated with a corresponding symptom but may, nonetheless, be indicative of the onset of motion sickness. Thus, the passenger module 220, in one approach, identifies the onset of motion sickness by identifying changes in the components that do not fully satisfy the thresholds for the symptoms but illustrate trends toward the thresholds. In various embodiments, the determination of the onset may include identifying trends in two or more components of the passenger state 260. In still further embodiments, the passenger module 220 determines the onset by correlating trends in one or more components with at least one other component that satisfies a threshold for a symptom. In either case, the passenger module 220, in one or more approaches, can not only identify when a passenger is experiencing developed motion sickness but also can detect an origination or onset of the symptoms. As such, the passenger module 220 can indicate either the onset or the presence of existing symptoms to the control module 230 to cause the control module 230 to perform various mitigating actions.

With continued reference to FIG. 2, in one embodiment, the control module 230 generally includes instructions that function to control the processor 110 to control one or more vehicle components when the passenger state 260 correlates with the symptoms. As indicated, the correlation of the passenger state 260 with the symptoms can include a direct satisfaction of the symptoms or, for example, an onset of the symptoms. In either case, the control module 230, in one approach, receives an indicator (e.g., an electronic signal) from the passenger module 220 specifying the condition and controls one or more vehicle systems/components in an attempt to mitigate the symptoms.

In one approach, the control module 230 controls a seat, an infotainment system, a radio, an environmental system, a display, movements of windows, a moon/sunroof, sunshades, or another component within the vehicle 100 with which the control module 230 can communicate to provide control instructions. In one embodiment, the control module 230 communicates with the various components and systems via a vehicle bus such as a controller area network (CAN) bus. In further approaches, the control module 230 communicates with the components/systems via wireless communications. Additionally, while the components/systems are generally discussed separately, in one approach, the control module 230 simultaneously controls two or more of the systems/components.

Furthermore, the control module 230 generally functions according to indications from the passenger module 220. That is, for example, the control module 230 receives indicators/signals of when the passenger is experiencing motion sickness. Thus, in response to the signals, the control module 230 controls the components/systems to mitigate the symptoms. In one or more embodiments, the signals are, for example, discrete signals that identify simply that the passenger is experiencing motion sickness. Additionally, or alternatively, the passenger module 220 provides signals indicating a position of the passenger within the vehicle 100, a severity of the symptoms, which systems have been identified, and/or other information that facilitates determinations by the control module 230.

Continuing with the control module 230 and control of the components/systems, in one embodiment, the display is a heads-up display, a display integrated with an infotainment system, an augmented reality (AR) display aligned with a windshield or other window within the vehicle 100, or another display within the vehicle 100 that is within a view of the passenger. Accordingly, the control module 230, in one approach, controls the display by causing a graphic to be displayed near a horizon line in a plane of view of the passenger. For example, where the display is situated as a heads-up display (HUD), an AR display integrated with the windshield or another window, the control module 230 causes a circle, dot, or other graphic to be shown within the display. The graphic provides a point of focus for the passenger near the horizon in order to calm the disassociation between senses of the passenger.

In one embodiment, the control module 230 controls the display by turning off the display in order to cause the passenger to look outside of the vehicle 100 instead of at a fixed point within the vehicle 100, which can exacerbate the symptoms by furthering the disassociation. For example, the control module 230 renders the focus point on a HUD while turning off or blacking out an infotainment display within a dash of the vehicle 100. In this way, the control module 230 induces the passenger to view the focus point and regain a sense of movement for the vehicle 100.

Moreover, the control module 230, in one embodiment, controls a seat of the passenger in response to the passenger module 220 identifying motion sickness. That is, the control module 230, in one arrangement, controls an actuator of the seat to cause the seat to recline thereby adjusting a position of the passenger into a supine position. Additionally, or alternatively, the control module 230, in one approach, adjusts a height of the seat, a lumbar support in the seat, a forward position of the seat, or another available functionality of the seat in order to mitigate the symptoms.

In one aspect, the control module 230 controls components of the vehicle 100 such as an infotainment system and/or a radio. For example, the control module 230 mutes sound from the devices in response to the passenger module 220 indicating the presence of symptoms. In a further approach, the control module 230 plays soothing sounds (e.g., ocean, rainforest, etc.).

In still further aspects, the control module 230 controls environmental systems of the vehicle 100 in response to the passenger module 220. As used herein, the environmental systems can include climate systems (e.g., HVAC also referred to as heating and air conditioning), seat warmers, seat ventilation, window actuators for raising/lowering windows, ionization, and so on. In general, the control module 230 controls the environmental systems to adjust temperature, fan speed, etc. in order to improve the comfort of the passenger. For example, when the passenger is experiencing symptoms such as perspiration and increased heart rate, the control module 230 adjusts the environmental systems by increasing fan speed, lowering the temperature, etc. in order to alter conditions around the passenger. In a further aspect, the control module 230 controls movements of windows, a moon/sunroof, and/or sunshades in combination with the environmental systems or separately. Thus, the control module 230 can open and/or close the windows and roof in order to further regulate an internal environment of the vehicle 100 around the passenger. The control module 230 can control the sun/moon roof and sunshades to adjust an amount of light/sun imparted on the passenger. In this way, the control module 230 facilitates mitigating the symptoms.

Moreover, the control module 230, in one approach, controls the various systems responsively to the passenger state 260. That is, as the passenger state 260 changes, the passenger module 220, in one arrangement, informs the control module 230 of the changes. Thus, by way of example, if the control module 230 initially reclines the seat and the passenger state 260 does not improve (e.g., the symptoms lessen below threshold values), then the control module 230, for example, proceeds with additional mitigating actions such as adjusting the temperature and fan speed.

Accordingly, the motion system 170, in one embodiment, dynamically reacts to the passenger state 260 to further adjust aspects of the vehicle 100 and take further actions or reverse actions previously taken. That is, in one approach, the control module 230 reverses control of the seat from a reclined position to an upright position upon, for example, indications from the passenger module 220 that the passenger state 260 has improved. In still further approaches, the control module 230 may reverse previously taken actions when, for example, the noted actions do not improve the condition or when the actions worsen the condition of the passenger. As one example, when the control module 230 reclines the passenger and the passenger module 230 indicates that the passenger state 260 worsens (e.g., additional symptoms appear, heart increases/spikes), then the control module 230 may return the seat to an original upright position and, for example, perform other mitigating actions such as displaying the focus point on a display and/or adjusting the climate controls.

In either case, the particular actions taken by the control module 230 can generally be varied according to a particular implementation. Thus, the control module 230 is, in one approach, programmable to perform preferred ones of the noted actions or not perform particular ones of the noted actions. In still further arrangements, the control module 230 implements a look-up table (LUT) that correlates the symptoms from the passenger state 260 with particular actions to be undertaken to mitigate the motion sickness. Thus, the control module 230 can implement various actions and combinations of actions depending on the passenger state 260 in order to mitigate motion sickness.

Figure 3:
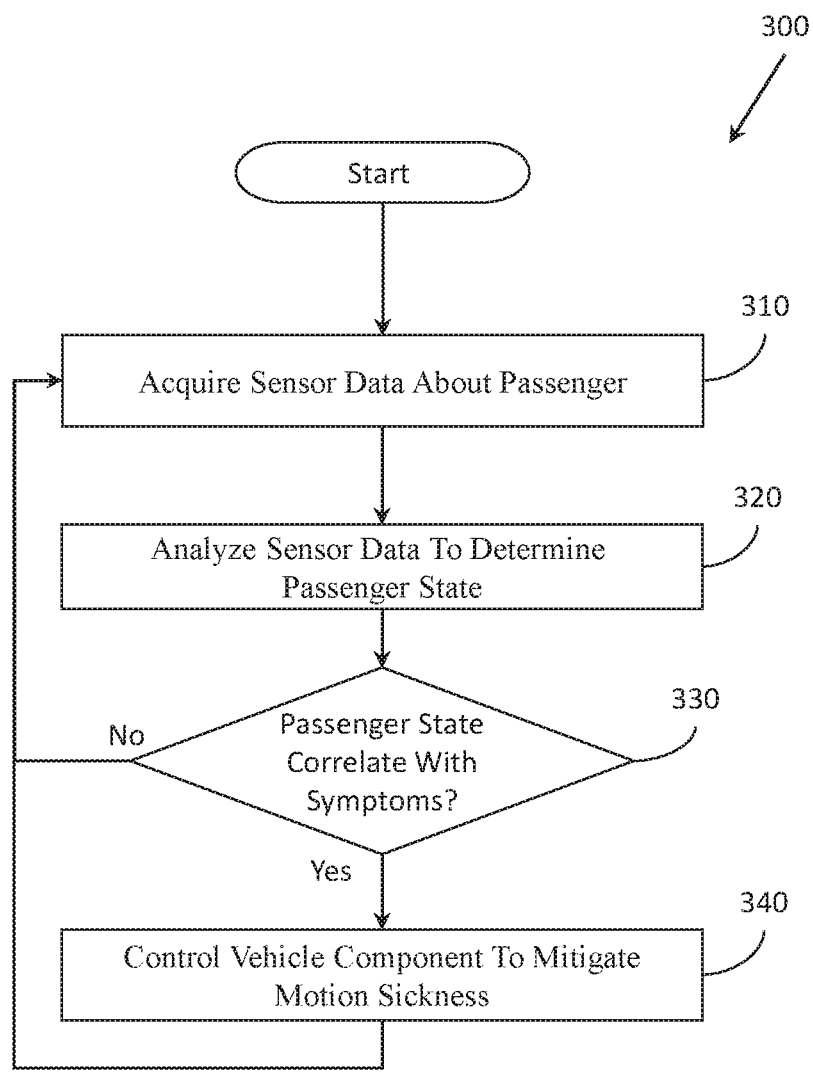
FIG. 3 illustrates one embodiment of a method associated with monitoring a passenger to identify symptoms of motion sickness and control at least one vehicle component to mitigate motion sickness in the passenger.

Additional aspects of mitigating motion sickness in a passenger of a vehicle will be discussed in relation to FIG. 3. FIG. 3 illustrates a method 300 associated with monitoring a passenger in a vehicle and selectively performing various actions to mitigate motion sickness. Method 300 will be discussed from the perspective of the motion system 170 of FIG. 1. While method 300 is discussed in combination with the motion system 170, it should be appreciated that the method 300 is not limited to being implemented within the motion system 170 but is instead one example of a system that may implement the method 300.

At 310, the passenger module 220 acquires the sensor data 250. In one embodiment, acquiring the sensor data 250 includes communicating with at least a wearable sensor worn or implanted on/in the passenger to acquire the sensor data 250. As noted previously, the wearable sensor may be worn or implanted by/in a passenger and provide information about vital signs of the passenger to the motion system 170. In further embodiments, the passenger module 220 additionally, or alternatively, acquires the sensor data 250 from further sensors in the vehicle 100 such as cameras, and other passenger monitoring sensors. The sensor data 250 generally indicates vital signs of the passenger including at least a heart rate. In further aspects, the sensor data 250 indicates a breathing rate, identification of whether the passenger is presently sweating, a blood pressure of the passenger, and other physical traits of the passenger.

Moreover, the sensor data 250, in one aspect, also indicates a position of the passenger within the vehicle 100 and can also specify a pose of the passenger such as head position, upper body position, arm positions, and so on. The motion system 170, in one embodiment, further uses the pose to infer aspects of the passenger state 260.

At 320, the passenger module 220 analyzes sensor data 250 about the passenger to produce a passenger state 260. As previously discussed, the passenger state 260 characterizes a current physical condition of the passenger while riding in the vehicle 100. Thus, the passenger state 260 characterizes aspects of the passenger such as vital signs and changes in vital signs over a period of time. In further aspects, the passenger state 260 indicates contextual aspects such as the pose of the passenger (e.g., reclined, bent over, head out window) that may be indicative of symptoms presently experienced by the passenger. In either case, the passenger module 220 analyzes the sensor data 250 using a set of models/functions that identify patterns and other information in order to resolve the passenger state 260 therefrom.

At 330, the passenger module 220 determines whether the passenger state 260 correlates with symptoms of motion sickness in the passenger. In one embodiment, the passenger module 220 compares the passenger state 260 with the symptoms to determine when an onset of the symptoms is occurring or when the symptoms are already developed in the passenger. The symptoms can include increases in a heart rate, a breathing rate, sweating, and a blood pressure of the passenger, and so on. Thus, when the passenger state 260 indicates the presence of, for example, two or more of the symptoms, the passenger module 220 indicates the presence of motion sickness and the control module 230 proceeds as discussed at block 340. However, if the passenger state 260 does not indicate the presence of the symptoms, then the passenger module 220 continues to monitor the passenger as discussed at blocks 310, 320, and 330.

At 340, the control module 230 controls at least one vehicle component/system responsive to a determination of the passenger module 220 at block 340. In one embodiment, the control module 230 adjusts a current configuration of the component/system relative to the passenger. That is, the control module 230, in one approach, considers the symptoms of the passenger as, for example, specified by the passenger state 260 or as indicated by the passenger module 220 and selects and adjusts one or more of the vehicle components according thereto.

In various approaches, the control module 230 changes a position of a seat in which the passenger is seated to improve comfort, adapt a view of the external environment (i.e., in order to better sense motion of the vehicle), and so on. Changing the position of the seat can include the control module 230 reclining the seat to permit the passenger to lay substantially supine (i.e., flat) in the seat. Furthermore, as previously discussed, the control module 230 can also control a display to present a marker/graphic for the passenger to view in order to focus the passenger on an area related to the motion of the vehicle. In a further aspect, the control module 230 can control the display while also, for example, adjusting a height/position of the seat to correlate a field-of-view of the passenger with the display (e.g., a HUD or AR display).

In a further aspect, the control module 230 controls a vehicle component such as environmental systems by adjusting the environmental systems to alter conditions around the passenger. Accordingly, when the symptoms indicate the passenger may be feeling hot or perspiring, the control module 230 can increase fan speeds, lower temperatures, open a window, and so on.

Because the method 300, in one embodiment, is an iterative process that the motion system 170 executes, the control module 230 may consider prior actions taken when selecting which components/systems to control in response to a present passenger state 260. That is, the symptoms of motion sickness may be progressive, and thus the control module 230 may elevate a response or reduce a response over time according to the passenger state 260. Thus, in one approach, the control module 230 progressively applies further actions as the symptoms progress. By way of example, the control module 230 may initially display the marker in an attempt to focus the passenger on the horizon and external environment of the vehicle 100. If the symptoms do not improve and the passenger module 220 further indicates additional symptoms to the control module 230, then the control module 230 may take further mitigating actions such as adjusting the environmental systems. Upon an even further progression, in one approach, the control module 230 may then recline the seat of the passenger. Accordingly, depending on the symptoms, the control module 230 can adjust a response to include control of a single component or multiple components. In either case, the motion system 170 actively monitors the passenger and automatically controls aspects of the vehicle 100 to mitigate motion sickness within a passenger.

Figure 4:
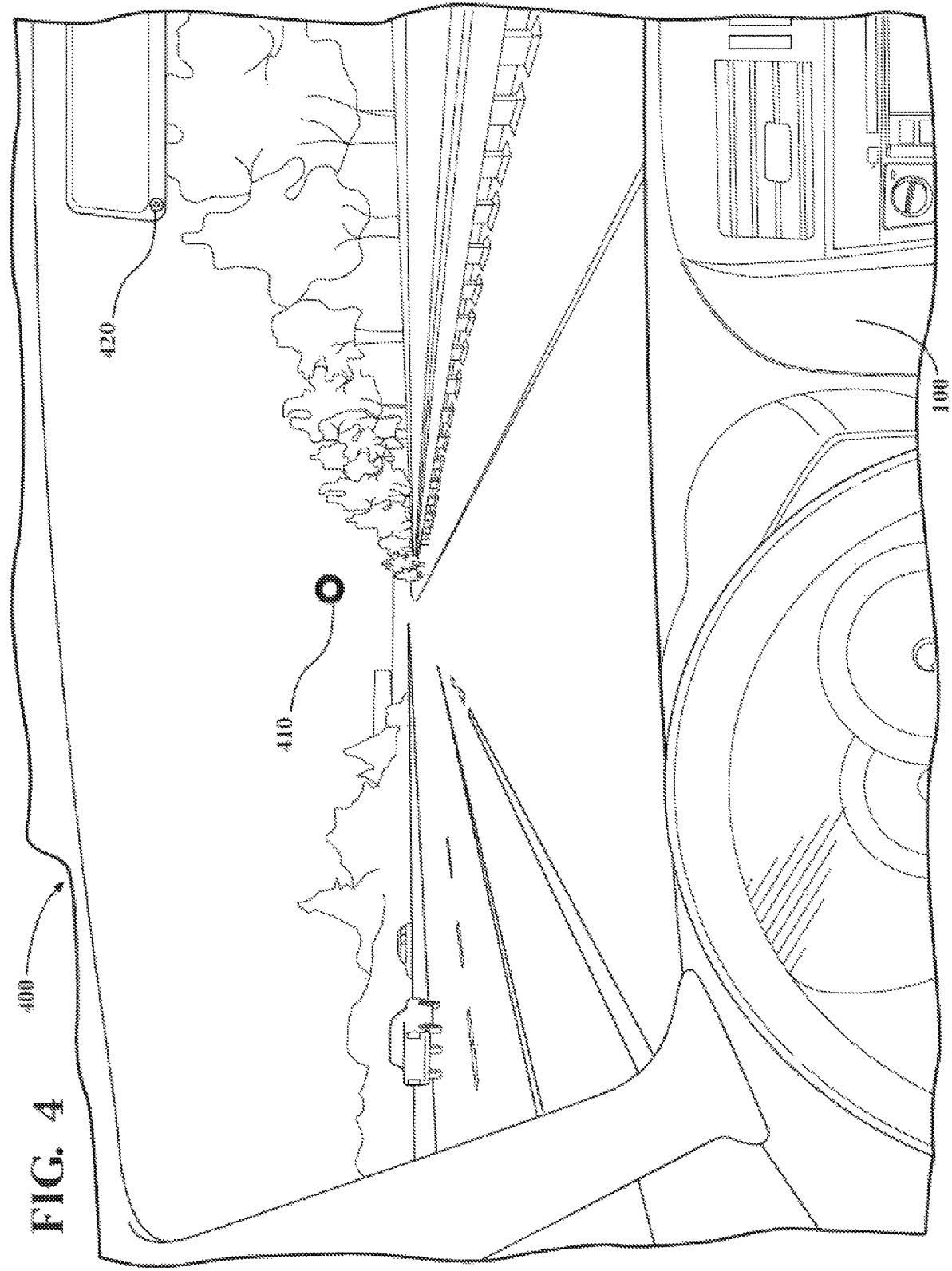
FIG. 4 illustrates one example of a marker as may be rendered in a display of a vehicle.
Figure 5:
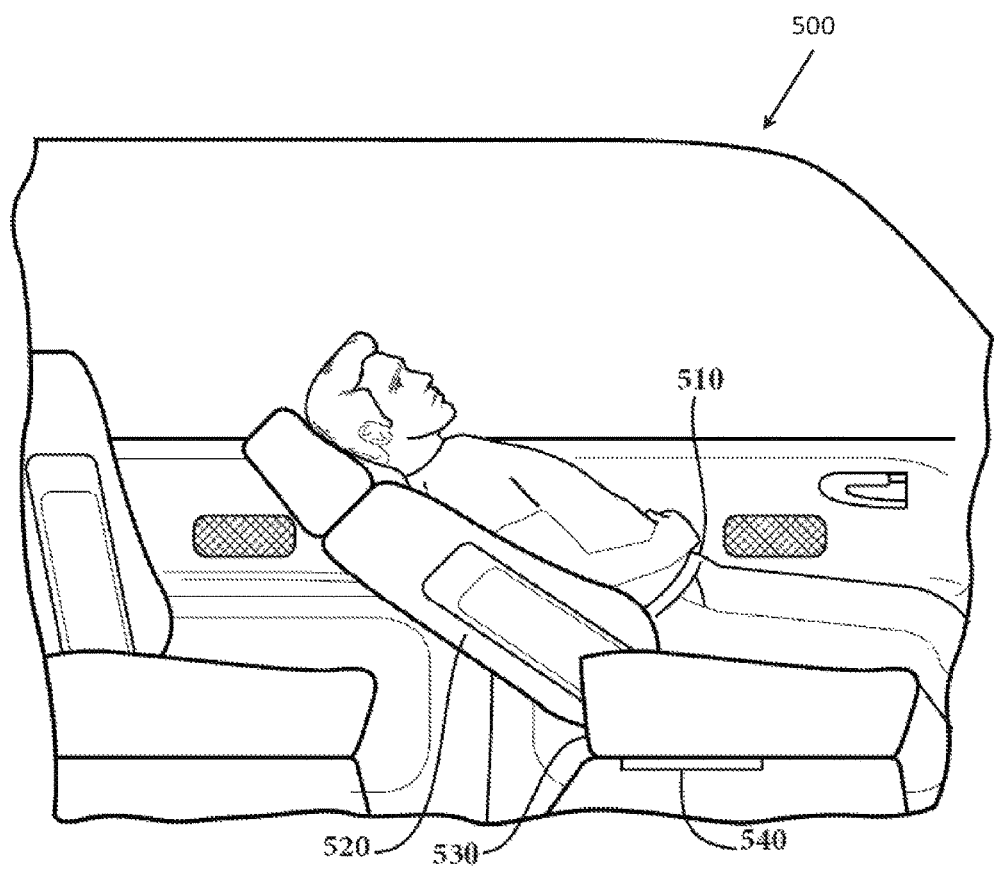
FIG. 5 is a diagram depicting a cutaway of a passenger compartment of a vehicle with a passenger in a supine position.

As a further explanation of various features implemented by the motion system 170, reference is now made to FIGS. 4 and 5. FIGS. 4 and 5 both illustrate actions undertaken by the motion system 170 to mitigate motion sickness within a passenger. FIG. 4 illustrates an interior view 400 of a passenger compartment of the vehicle 100. It should be noted that the view 400 is from a perspective of a seat of an operator behind a steering wheel, however, the motion system 170 can generally monitor and control aspects of the vehicle 100 in relation to a passenger seated in any position within the vehicle 100. Moreover, when applied to an operator of the vehicle 100, the motion system 170 may limit the implemented actions (e.g., avoid reclining the seat) unless the vehicle 100 is operating, for example, in an autonomous mode as identified by the motion system 170. In either case, the control module 230, in one example, controls a display such as an AR display integrated with a windshield to display a marker 410. The control module 230 generates the marker 410 near a horizon line of the external environment according to a perspective of the passenger.

Thus, the control module 230 may use a camera 420 within the vehicle 100 to track a head/eyes of the passenger in determining the perspective. In either case, the control module 230 can render a graphic such as the marker 410 on a display in order to focus the passenger on the external environment and motion of the vehicle 100 in an attempt to mitigate the symptoms. FIG. 5 illustrates a cutaway view 500 of a passenger compartment of the vehicle 100. As shown in FIG. 5 a passenger 510 is reclined in a seat. The seat includes a seat back 520, a seat bottom 530, and a seat module 540. The seat module 540 controls actuators within the seat back 520 and seat bottom 530 to adjust a position of the seat. Thus, as shown, the control module 230 has provided control signals to the seat module 540 to control the seat back 520 to recline. As previously mentioned, in further aspects, the control module 230 can adjust a height of the seat by, for example, providing signals to the seat module 540 to cause the seat bottom 530 to raise or lower. Similarly, the control module 230 can provide signals to control lumbar supports, seat heaters, seat ventilation, and so on. In this way, the motion system 170 improves the handling of motion sickness through monitoring and executing various actions to mitigate the symptoms of motion sickness in passengers.

Additionally, it should be appreciated that the motion system 170 from FIG. 1 can be configured in various arrangements with separate integrated circuits and/or chips. In such embodiments, the passenger module 220 is embodied as a separate integrated circuit. Additionally, the control module 230 is embodied on an individual integrated circuit. The circuits are connected via connection paths to provide for communicating signals between the separate circuits. Of course, while separate integrated circuits are discussed, in various embodiments, the circuits may be integrated into a common integrated circuit board. Additionally, the integrated circuits may be combined into fewer integrated circuits or divided into more integrated circuits. In another embodiment, the modules 220 and 230 may be combined into a separate application-specific integrated circuit. In further embodiments, portions of the functionality associated with the modules 220 and 230 may be embodied as firmware executable by a processor and stored in a non-transitory memory. In still further embodiments, the modules 220 and 230 are integrated as hardware components of the processor 110.

In another embodiment, the described methods and/or their equivalents may be implemented with computer-executable instructions. Thus, in one embodiment, a non-transitory computer-readable medium is configured with stored computer executable instructions that when executed by a machine (e.g., processor, computer, and so on) cause the machine (and/or associated components) to perform the method.

While for purposes of simplicity of explanation, the illustrated methodologies in the figures are shown and described as a series of blocks, it is to be appreciated that the methodologies (e.g., method 300 of FIG. 3) are not limited by the order of the blocks, as some blocks can occur in different orders and/or concurrently with other blocks from that shown and described. Moreover, less than all the illustrated blocks may be used to implement an example methodology. Blocks may be combined or separated into multiple components. Furthermore, additional and/or alternative methodologies can employ additional blocks that are not illustrated.

FIG. 1 will now be discussed in full detail as an example environment within which the system and methods disclosed herein may operate. In some instances, the vehicle 100 is configured to switch selectively between an autonomous mode, one or more semi-autonomous operational modes, and/or a manual mode. Such switching can be implemented in a suitable manner. "Manual mode" means that all of or a majority of the navigation and/or maneuvering of the vehicle is performed according to inputs received from a user (e.g., human driver).

In one or more embodiments, the vehicle 100 is an autonomous vehicle. As used herein, "autonomous vehicle" refers to a vehicle that operates in an autonomous mode. "Autonomous mode" refers to navigating and/or maneuvering the vehicle 100 along a travel route using one or more computing systems to control the vehicle 100 with minimal or no input from a human driver. In one or more embodiments, the vehicle 100 is fully automated. In one embodiment, the vehicle 100 is configured with one or more semi-autonomous operational modes in which one or more computing systems perform a portion of the navigation and/or maneuvering of the vehicle 100 along a travel route, and a vehicle operator (i.e., driver) provides inputs to the vehicle to perform a portion of the navigation and/or maneuvering of the vehicle 100 along a travel route. Such semi-autonomous operation can include supervisory control to ensure the vehicle 100 remains within defined state constraints.

The vehicle 100 can include one or more processors 110. In one or more arrangements, the processor(s) 110 can be a main processor of the vehicle 100. For instance, the processor(s) 110 can be an electronic control unit (ECU). The vehicle 100 can include one or more data stores 115 (e.g., data store 240) for storing one or more types of data. The data store 115 can include volatile and/or non-volatile memory. Examples of suitable data stores 115 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store 115 can be a component of the processor(s) 110, or the data store 115 can be operatively connected to the processor(s) 110 for use thereby. The term "operatively connected," as used throughout this description, can include direct or indirect connections, including connections without direct physical contact.

In one or more arrangements, the one or more data stores 115 can include map data. The map data can include maps of one or more geographic areas. In some instances, the map data can include information (e.g., metadata, labels, etc.) on roads, traffic control devices, road markings, structures, features, and/or landmarks in the one or more geographic areas. In some instances, the map data can include aerial/satellite views. In some instances, the map data can include ground views of an area, including 360-degree ground views. The map data can include measurements, dimensions, distances, and/or information for one or more items included in the map data and/or relative to other items included in the map data. The map data 116 can include a digital map with information about road geometry. The map data can further include feature-based map data such as information about relative locations of buildings, curbs, poles, etc. In one or more arrangements, the map data can include one or more terrain maps. In one or more arrangements, the map data can include one or more static obstacle maps. The static obstacle map(s) 118 can include information about one or more static obstacles located within one or more geographic areas. A "static obstacle" is a physical object whose position does not change or substantially change over a period of time and/or whose size does not change or substantially change over a period of time. Examples of static obstacles include trees, buildings, curbs, fences, railings, medians, utility poles, statues, monuments, signs, benches, furniture, mailboxes, large rocks, hills. The static obstacles can be objects that extend above ground level.

The one or more data stores 115 can include sensor data (e.g., sensor data 250). In this context, "sensor data" means any information from the sensors that the vehicle 100 is equipped with, including the capabilities and other information about such sensors.

As noted above, the vehicle 100 can include the sensor system 120. The sensor system 120 can include one or more sensors. "Sensor" means any device, component and/or system that can detect, perceive, and/or sense something. The one or more sensors can be configured to operate in real-time. As used herein, the term "real-time" means a level of processing responsiveness that a user or system senses as sufficiently immediate for a particular process or determination to be made, or that enables the processor to keep up with some external process.

In arrangements in which the sensor system 120 includes a plurality of sensors, the sensors can work independently from each other. Alternatively, two or more of the sensors can work in combination with each other. In such a case, the two or more sensors can form a sensor network. The sensor system 120 and/or the one or more sensors can be operatively connected to the processor(s) 110, the data store(s) 115, and/or another element of the vehicle 100 (including any of the elements shown in FIG. 1). The sensor system 120 can acquire data of at least a portion of the external environment of the vehicle 100.

The sensor system 120 can include any suitable type of sensor. Various examples of different types of sensors will be described herein. However, it will be understood that the embodiments are not limited to the particular sensors described. The sensor system 120 can include one or more vehicle sensors 121. The vehicle sensor(s) 121 can detect and/or sense information about the vehicle 100 itself or interior compartments of the vehicle 100. In one or more arrangements, the vehicle sensor(s) 121 can be configured to detect, and/or sense position and orientation changes of the vehicle 100, such as, for example, based on inertial acceleration. In one or more arrangements, the vehicle sensor(s) 121 can include one or more accelerometers, one or more gyroscopes, an inertial measurement unit (IMU), a dead-reckoning system, a global navigation satellite system (GNSS), a global positioning system (GPS), a navigation system, internal cameras, integrated sensors within one or more seats for monitoring passengers, and/or other suitable sensors. The vehicle sensor(s) 121 can be configured to detect, and/or sense one or more characteristics of the vehicle 100. In one or more arrangements, the vehicle sensor(s) 121 can include a speedometer to determine a current speed of the vehicle 100. Moreover, the vehicle sensor system 121 can include sensors throughout a passenger compartment such as pressure/weight sensors in seats, seatbelt sensors, camera(s), and so on.

Alternatively, or in addition, the sensor system 120 can include one or more environment sensors 122 configured to acquire, and/or sense driving environment data. "Driving environment data" includes data or information about the external environment in which an autonomous vehicle is located or one or more portions thereof. For example, the one or more environment sensors 122 can be configured to detect and/or sense obstacles in at least a portion of the external environment of the vehicle 100 and/or information/data about such obstacles. Such obstacles may be stationary objects and/or dynamic objects. The one or more environment sensors 122 can be configured to detect, and/or sense other things in the external environment of the vehicle 100, such as, for example, lane markers, signs, traffic lights, traffic signs, lane lines, crosswalks, curbs proximate the vehicle 100, off-road objects, etc.

Various examples of sensors of the sensor system 120 will be described herein. The example sensors may be part of the one or more environment sensors 122 and/or the one or more vehicle sensors 121. However, it will be understood that the embodiments are not limited to the particular sensors described. As an example, in one or more arrangements, the sensor system 120 can include one or more radar sensors, one or more LIDAR sensors, one or more sonar sensors, and/or one or more cameras. In one or more arrangements, the one or more cameras can be high dynamic range (HDR) cameras or infrared (IR) cameras.

The vehicle 100 can include an input system 130. An "input system" includes, without limitation, devices, components, systems, elements or arrangements or groups thereof that enable information/data to be entered into a machine. The input system 130 can receive an input from a vehicle passenger (e.g., an operator or a passenger). The vehicle 100 can include an output system 140. An "output system" includes any device, component, or arrangement or groups thereof that enable information/data to be presented to a vehicle passenger (e.g., a person, a vehicle passenger, etc.).

The vehicle 100 can include one or more vehicle systems 150. Various examples of the one or more vehicle systems 150 are shown in FIG. 1, however, the vehicle 100 can include a different combination of systems than illustrated in the provided example. In one example, the vehicle 100 can include a propulsion system, a braking system, a steering system, throttle system, a transmission system, a signaling system, a navigation system, and so on. The noted systems can separately or in combination include one or more devices, components, and/or a combination thereof.

By way of example, the navigation system can include one or more devices, applications, and/or combinations thereof configured to determine the geographic location of the vehicle 100 and/or to determine a travel route for the vehicle 100. The navigation system can include one or more mapping applications to determine a travel route for the vehicle 100. The navigation system can include a global positioning system, a local positioning system or a geolocation system.

The processor(s) 110, the motion system 170, and/or the autonomous driving system 160 can be operatively connected to communicate with the various vehicle systems 150 and/or individual components thereof. For example, returning to FIG. 1, the processor(s) 110 and/or the autonomous driving system 160 can be in communication to send and/or receive information from the various vehicle systems 150 to control the movement, speed, maneuvering, heading, direction, etc. of the vehicle 100. The processor(s) 110, the motion system 170, and/or the autonomous driving system 160 may control some or all of these vehicle systems 150 and, thus, may be partially or fully autonomous.

The processor(s) 110, the motion system 170, and/or the autonomous driving system 160 can be operatively connected to communicate with the various vehicle systems 150 and/or individual components thereof. For example, returning to FIG. 1, the processor(s) 110, the motion system 170, and/or the autonomous driving system 160 can be in communication to send and/or receive information from the various vehicle systems 150 to control the movement, speed, maneuvering, heading, direction, etc. of the vehicle 100. The processor(s) 110, the motion system 170, and/or the autonomous driving system 160 may control some or all of these vehicle systems 150.

The processor(s) 110, the motion system 170, and/or the autonomous driving system 160 may be operable to control the navigation and/or maneuvering of the vehicle 100 by controlling one or more of the vehicle systems 150 and/or components thereof. For instance, when operating in an autonomous mode, the processor(s) 110, the motion system 170, and/or the autonomous driving system 160 can control the direction and/or speed of the vehicle 100. The processor(s) 110, the motion system 170, and/or the autonomous driving system 160 can cause the vehicle 100 to accelerate (e.g., by increasing the supply of energy provided to the engine), decelerate (e.g., by decreasing the supply of energy to the engine and/or by applying brakes) and/or change direction (e.g., by turning the front two wheels).

Moreover, the motion system 170 and/or the autonomous driving system 160 can function to perform various driving-related tasks such as parking the vehicle 100. That is, in one embodiment, the motion system 170, and/or the autonomous driving system 160 function to identify a suitable parking location and maneuver the vehicle 100 to the parking location/spot. In various approaches, this auto-parking functionality may further include communicating with one or more infrastructure devices (e.g., parking meters/systems) to pay fees, locate parking spots, and so on.

The vehicle 100 can include one or more actuators. The actuators can be any element or combination of elements operable to modify, adjust and/or alter one or more of the vehicle systems or components thereof to responsive to receiving signals or other inputs from the processor(s) 110 and/or the autonomous driving system 160. Any suitable actuator can be used. For instance, the one or more actuators can include motors, pneumatic actuators, hydraulic pistons, relays, solenoids, and/or piezoelectric actuators, just to name a few possibilities.

The vehicle 100 can include one or more modules, at least some of which are described herein. The modules can be implemented as computer-readable program code that, when executed by a processor 110, implement one or more of the various processes described herein. One or more of the modules can be a component of the processor(s) 110, or one or more of the modules can be executed on and/or distributed among other processing systems to which the processor(s) 110 is operatively connected. The modules can include instructions (e.g., program logic) executable by one or more processor(s) 110. Alternatively, or in addition, one or more data store 115 may contain such instructions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

The vehicle 100 can include one or more autonomous driving systems 160. The autonomous driving system 160 can be configured to receive data from the sensor system 120 and/or any other type of system capable of capturing information relating to the vehicle 100 and/or the external environment of the vehicle 100. In one or more arrangements, the autonomous driving system 160 can use such data to generate one or more driving scene models. The autonomous driving system 160 can determine position and velocity of the vehicle 100. The autonomous driving system 160 can determine the location of obstacles, obstacles, or other environmental features including traffic signs, trees, shrubs, neighboring vehicles, pedestrians, etc.

The autonomous driving system 160 can be configured to receive, and/or determine location information for obstacles within the external environment of the vehicle 100 for use by the processor(s) 110, and/or one or more of the modules described herein to estimate position and orientation of the vehicle 100, vehicle position in global coordinates based on signals from a plurality of satellites, or any other data and/or signals that could be used to determine the current state of the vehicle 100 or determine the position of the vehicle 100 with respect to its environment for use in either creating a map or determining the position of the vehicle 100 in respect to map data.

The autonomous driving system 160 either independently or in combination with the motion system 170 can be configured to determine travel path(s), current autonomous driving maneuvers for the vehicle 100, future autonomous driving maneuvers and/or modifications to current autonomous driving maneuvers based on data acquired by the sensor system 120, driving scene models, and/or data from any other suitable source such as determinations from the sensor data 250 as implemented by the motion system 170. "Driving maneuver" means one or more actions that affect the movement of a vehicle. Examples of driving maneuvers include: accelerating, decelerating, braking, turning, moving in a lateral direction of the vehicle 100, changing travel lanes, merging into a travel lane, and/or reversing, just to name a few possibilities. The autonomous driving system 160 can be configured can be configured to implement determined driving maneuvers. The autonomous driving system 160 can cause, directly or indirectly, such autonomous driving maneuvers to be implemented. As used herein, "cause" or "causing" means to make, command, instruct, and/or enable an event or action to occur or at least be in a state where such event or action may occur, either in a direct or indirect manner. The autonomous driving system 160 can be configured to execute various vehicle functions and/or to transmit data to, receive data from, interact with, and/or control the vehicle 100 or one or more systems thereof (e.g., one or more of vehicle systems 150).

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-5, but the embodiments are not limited to the illustrated structure or application.

The flowcharts and block diagrams in the figures illustrate the architecture, functionality, and operation of possible implementations of systems, methods, and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Examples of such a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read. In the context of this document, a computer-readable storage medium may be any tangible medium that can contain, or store a program for use by or in connection with an instruction execution system, apparatus, or device.

The following includes definitions of selected terms employed herein. The definitions include various examples and/or forms of components that fall within the scope of a term and that may be used for various implementations. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Module," as used herein, includes a computer or electrical hardware component(s), firmware, a non-transitory computer-readable medium that stores instructions, and/or combinations of these components configured to perform a function(s) or an action(s), and/or to cause a function or action from another logic, method, and/or system. Module may include a microprocessor controlled by an algorithm, a discrete logic (e.g., ASIC), an analog circuit, a digital circuit, a programmed logic device, a memory device including instructions that when executed perform an algorithm, and so on. A module, in one or more embodiments, includes one or more CMOS gates, combinations of gates, or other circuit components. Where multiple modules are described, one or more embodiments include incorporating the multiple modules into one physical module component. Similarly, where a single module is described, one or more embodiments distribute the single module between multiple physical components.

Additionally, module as used herein includes routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™ Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A motion system for mitigating motion sickness in a passenger of a vehicle, comprising:
   one or more processors;
   a memory communicably coupled to the one or more processors and storing:
   a passenger module including instructions that when executed by the one or more processors cause the one or more processors to analyze sensor data about the passenger to produce a passenger state that characterizes a current physical condition of the passenger while riding in the vehicle,
   wherein the passenger module includes instructions to determine whether the passenger state correlates with symptoms of motion sickness in the passenger; and
   a control module including instructions that when executed by the one or more processors cause the one or more processors to control, in the vehicle, a vehicle component to adjust a current configuration relative to the passenger when the passenger state correlates with the symptoms, wherein the control module includes instructions to control the vehicle component including instructions to automatically change, in response to determining the passenger state correlates with the symptoms of motion sickness, a position of a seat in which the passenger is seated.

2. The motion system of claim 1, wherein the control module includes instructions to change the position of the seat including instructions to cause the seat to recline to permit the passenger to lay supine in the seat.

3. The motion system of claim 1, wherein the passenger module includes instructions to acquire the sensor data from at least a wearable sensor of the passenger, the wearable sensor communicating with the passenger module to provide the sensor data, wherein the sensor data indicates vital signs of the passenger including at least a heart rate, and
   wherein the passenger module includes instructions to analyze the sensor data to produce the passenger state including instructions to characterize the vital signs over a defined time period to assess changes in the passenger that are indicative of motion sickness.

4. The motion system of claim 3, wherein the passenger module includes instructions to acquire the sensor data including instructions to acquire at least a portion of the sensor data from one or more integrated sensors of the vehicle, the one or more integrated sensors including a camera with a field-of-view of a passenger compartment of the vehicle, and
   wherein the sensor data includes a breathing rate, identification of whether the passenger is presently sweating, a blood pressure of the passenger, and physical traits of the passenger.

5. The motion system of claim 1, wherein the passenger module includes instructions to determine whether the passenger state correlates with the symptoms including instructions to compare the passenger state with the symptoms to determine when the passenger state corresponds with one or more of an onset of the symptoms and the symptoms being developed in the passenger, and
   wherein the symptoms include increases in a heart rate, a breathing rate, sweating, and a blood pressure of the passenger.

6. The motion system of claim 1, wherein the control module includes instructions to control the vehicle component including instructions to display, on a display of the vehicle, a marker for the passenger to view in order to focus the passenger on an area related to motion of the vehicle, and
   wherein the display is located along a horizon line in a plane of view of the passenger.

7. The motion system of claim 1, wherein the control module includes instructions to control the vehicle component including instructions to automatically adjust environmental systems in the vehicle to alter conditions around the passenger including at least ionization settings,
   wherein the environmental systems include one or more of seat heating, seat cooling, heater temperature, fan speed, cooling temperature, window position, air intake selection, and the ionization settings, and
   wherein the vehicle operates autonomously without manual control inputs from an operator.

8. A non-transitory computer-readable medium storing instructions for mitigating motion sickness in a passenger of a vehicle and that when executed by one or more processors cause the one or more processors to:
   analyze sensor data about the passenger to produce a passenger state that characterizes a current physical condition of the passenger while riding in the vehicle;
   determine whether the passenger state correlates with symptoms of motion sickness in the passenger; and
   control, in the vehicle, a vehicle component to adjust a current configuration relative to the passenger when the passenger state correlates with the symptoms, wherein the instructions to control the vehicle component include instructions to automatically change, in response to determining the passenger state correlates with the symptoms of motion sickness, a position of a seat in which the passenger is seated.

9. The non-transitory computer-readable medium of claim 8, wherein the instructions to acquire the sensor data include instructions to communicate with a wearable sensor worn by the passenger, wherein the sensor data indicates vital signs of the passenger including at least a heart rate, and
   wherein the instructions to analyze the sensor data include instructions to characterize the vital signs over a defined time period to assess changes in the passenger that are indicative of motion sickness.

10. The non-transitory computer-readable medium of claim 9, wherein the instructions to acquire the sensor data include instructions to acquire at least a portion of the sensor data from one or more integrated sensors of the vehicle, the one or more integrated sensors including a camera with a field-of-view of a passenger compartment of the vehicle, and wherein the sensor data includes a breathing rate, identification of whether the passenger is presently sweating, a blood pressure of the passenger, and physical traits of the passenger.

11. A method of mitigating motion sickness in a passenger of a vehicle, comprising:

analyzing sensor data about the passenger to produce a passenger state that characterizes a current physical condition of the passenger while riding in the vehicle;

determining whether the passenger state correlates with symptoms of motion sickness in the passenger; and controlling, by a controller in the vehicle, a vehicle component to adjust a current configuration relative to the passenger when the passenger state correlates with the symptoms, wherein controlling the vehicle component includes automatically changing, in response to determining the passenger state correlates with the symptoms of motion sickness, a position of a seat in which the passenger is seated.

12. The method of claim 11, wherein changing the position of the seat includes reclining the seat to permit the passenger to lay supine in the seat.

13. The method of claim 11, further comprising:

acquiring the sensor data from at least a wearable sensor of the passenger, the wearable sensor communicating with the vehicle to provide the sensor data, wherein the sensor data indicates vital signs of the passenger including at least a heart rate, and wherein analyzing the sensor data to produce the passenger state includes characterizing the vital signs over a defined time period to assess changes in the passenger that are indicative of motion sickness.

14. The method of claim 13, wherein acquiring the sensor data includes acquiring at least a portion of the sensor data from one or more integrated sensors of the vehicle, the one or more integrated sensors including a camera with a field-of-view of a passenger compartment of the vehicle, and wherein the sensor data includes a breathing rate, identification of whether the passenger is presently sweating, a blood pressure of the passenger, and physical traits of the passenger.

15. The method of claim 11, wherein determining whether the passenger state correlates with the symptoms includes comparing the passenger state with the symptoms to determine when the passenger state corresponds with one or more of an onset of the symptoms and the symptoms being developed in the passenger, and wherein the symptoms include increases in a heart rate, a breathing rate, sweating, and a blood pressure of the passenger.

16. The method of claim 11, wherein controlling the vehicle component includes displaying, on a display of the vehicle, a marker for the passenger to view in order to focus the passenger on an area related to motion of the vehicle, and wherein the display is located along a horizon line in a plane of view of the passenger.

17. The method of claim 11, wherein controlling the vehicle component includes automatically adjusting environmental systems in the vehicle to alter conditions around the passenger including at least ionization settings, and wherein the environmental systems include one or more of seat heating, seat cooling, heater temperature, fan speed, cooling temperature, window position, air intake selection, and the ionization settings.

* * * * *